United States Patent [19]

Wegman et al.

[11] Patent Number: 4,594,463

[45] Date of Patent: Jun. 10, 1986

[54] SYNTHESIS OF ALDEHYDES FROM ALCOHOLS

[75] Inventors: Richard W. Wegman, South Charleston; Deborah S. Miller, Charleston, both of W. Va.

[73] Assignee: Union Carbide Corporation, Danbury, Conn.

[21] Appl. No.: 695,370

[22] Filed: Jan. 28, 1985

[51] Int. Cl.$^4$ .............................................. C07C 45/49
[52] U.S. Cl. ............................ 568/487; 568/496; 568/902
[58] Field of Search .................... 568/487, 496, 902

[56] References Cited

U.S. PATENT DOCUMENTS

| | | | |
|---|---|---|---|
| 3,511,885 | 5/1970 | Hughes | 260/666 |
| 3,752,859 | 8/1973 | Schell | 260/604 |
| 3,769,329 | 10/1973 | Paulik et al. | 560/232 |
| 3,825,601 | 7/1974 | Rennick | 260/604 |
| 3,919,324 | 11/1975 | Himmele et al. | 260/602 |
| 3,946,082 | 3/1976 | McVicker | 260/601 |
| 4,151,208 | 4/1979 | Pretzer et al. | 260/601 |
| 4,193,942 | 3/1980 | Gerritset et al. | 260/604 |
| 4,221,744 | 9/1980 | Unruh | 568/454 |
| 4,230,641 | 10/1980 | Bartish | 568/454 |
| 4,247,486 | 1/1981 | Brewester | 568/454 |
| 4,258,214 | 3/1981 | Hahramann et al. | 568/454 |
| 4,259,530 | 3/1981 | Matsushima et al. | 568/454 |
| 4,260,828 | 4/1981 | Morrell et al. | 568/454 |
| 4,262,141 | 4/1981 | Richter et al. | 568/454 |
| 4,262,142 | 4/1981 | Sherman et al. | 568/454 |
| 4,262,154 | 4/1981 | Gane et al. | 568/902 |
| 4,273,936 | 6/1981 | Fiato et al. | 562/606 |
| 4,275,243 | 6/1981 | Saito | 568/496 |
| 4,277,627 | 7/1981 | Bryant et al. | 568/454 |
| 4,288,558 | 9/1981 | Schmidt et al. | 518/716 |
| 4,319,043 | 3/1982 | Cook et al. | 568/902 |
| 4,351,964 | 9/1982 | Nakamura et al. | 568/484 |
| 4,361,707 | 11/1982 | Habib et al. | 568/487 |
| 4,374,752 | 2/1983 | Argento et al. | 568/487 |
| 4,390,729 | 6/1983 | Oswald | 568/454 |
| 4,405,815 | 9/1983 | Keim et al. | 568/487 |
| 4,433,176 | 2/1984 | Lin | 568/487 |
| 4,446,074 | 5/1984 | Jamerson et al. | 260/429 |
| 4,507,508 | 3/1985 | Hayden et al. | 568/487 |

OTHER PUBLICATIONS

Flakley et al., "Applied Catalysis", vol. 5 (1983), p. 5.

Primary Examiner—Werren B. Lone
Attorney, Agent, or Firm—E. Lieberstein

[57] ABSTRACT

A catalyst has been found for the low pressure hydroformylation of alcohols to produce aldehydes. This catalyst consists of a rhodium containing compound, an iodide containing compound, and a chelating Group V compound, which is used alone or in combination with a monodentate, Group V compound.

It is the first rhodium-based catalyst that generates acetaldehyde via hydroformylation of the methanol. The reaction is typically carried out at 160°–180° C. and 1000–2000 psi. The acetaldehyde rate and selectivity are 1–5 Mhr$^{-1}$ and 50–75%. Conventional cobalt catalysts require operating pressures of at least 3000–6000 psi in order to obtain reasonable productivities.

18 Claims, No Drawings

SYNTHESIS OF ALDEHYDES FROM ALCOHOLS

BACKGROUND OF THE INVENTION

This invention pertains to the synthesis of aldehydes from alcohols and more particularly to the low pressure reductive carbonylation of alcohols with a rhodium based catalyst.

BACKGROUND ART

The production of organic compounds using synthesis gas, which is a mixture of carbon monoxide and hydrogen, or from carbon monoxide as one of the reactants has been known for a significant period of time. It is well known that one can produce methanol directly from synthesis gas and that methanol can be further reacted by hydroformylation, homologation and carbonylation reactions to produce acetaldehyde, ethanol and acetic acid or its methyl ester, respectively. It is also known that alcohols, esters, ethers, and other organic compounds can be reacted with synthesis gas or carbon monoxide to produce oxygenated organic compounds. The difficulties, however, have resided in the ability to carry out any one of these chosen reactions to produce the desired compound at acceptable efficiency, conversion rate and selectivity.

In almost all instances the reaction is generally catalyzed using a Group VIII transition metal compound as catalyst and a halogen as the promoter. It is known that many other metal compounds and promoters can be used. In addition, the prior art has disclosed the use of secondary activators or ligands in conjunction with the metal catalysts and promoters. These secondary activators can be other metallic salts or compounds, amines, phosphorus compounds, as well as a multitude of other compounds that have been disclosed in the published literature. Thus, a typical catalyst system contains the metal atom catalyst, promoter and, optionally, ligands, solvents and secondary activators. Though a significant amount of literature does exist describing the production of aldehydes, to our knowledge it does not disclose or suggest our invention.

In the case of methanol hydroformylation/homologation, the reaction is catalyzed by several Group VIII transition metals used in conjunction with a halogen promoter. By far, cobalt has received the most attention as the Group VIII metal. Halogen compounds (covalent or ionic containing Cl, Br, or I (example $CH_3Z$, where $Z=Cl$, Br, I) promote the reaction. However, those compounds using I work the best. In addition to a catalyst consisting of a cobalt species and, an iodide promoter, (Co-I), a monodentate compound, $ER_3$, where $E=N$, P, As, Sb, or Bi and R is an organic moiety, can also be utilized. In most instances, the presence of $ER_3$ enhances the selectivity to the desired organic product. Thus, a typical catalyst utilized for the hydroformylation or homologation of methanol consists of $Co-I-ER_3$.

As mentioned above, numerous patents have issued dealing with cobalt-based catalysts for hydroformylation of methanol to acetaldehyde.

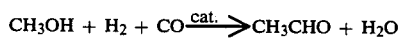

Only representative examples of the various types of cobalt catalysts will be summarized here. In general, Co, Co-I, and $Co-I-ER_3$ have been reported. Operating conditions are typically 160°–220° C. and 3000–6000 psi. Iodides increase rate and selectivity to acetaldehyde. $ER_3$ usually improve selectivity and are known to inhibit corrosion. Solvents are employed in some cases. They generally aid in increased acetaldehyde selectivity.

U.S. Pat. No. 4,201,868 to Celanese (May 1980) discloses a $Co-NR_3$ catalyst (halide free). Operating conditions are 175°–215° C. and 3000–6000 psi. Acetaldehyde yields are less than 35% and rates are less than 1.0 $Mhr^{-1}$.

U.S. Pat. No. 4,239,705 to Gulf (December 1980) discloses a $Co-I-AsR_3$ or $Co-I-SbR_3$ catalyst. Operating conditions are 200° C. and 4000 psi. Acetaldehyde rates and selectivities are 3.0 $Mhr^{-1}$ and 60%.

European Pat. No. 22735 to Rhone-Poulenc (January 1981) discloses a $Co-Ru-Cx-Mx$ catalyst where Cx is a covalent halide such as $CH_3I$ and Mx is an ionic halide such as NaI. The reaction is carried out at 185°–205° C. and 3550 psi. Acetaldehyde rates and selectivities are 4.0–6.0 $Mhr^{-1}$ and 85%.

U.S. Pat. No. 4,361,707 to Gulf (November 1982). This patent discloses the use of numerous chelating phosphine ligands utilized in combination with a Co-I catalyst. The reaction is carried out at 200° C. and 4000 psi. Acetaldehyde rates and selectivities are 6 $Mhr^{-1}$ and 50%.

An effective rhodium-based catalyst for the hydroformylation of methanol to acetaldehyde has not been reported in the literature. However, it is well known that a rhodium-based catalyst will catalyze the carbonylation of methanol to acetic acid.

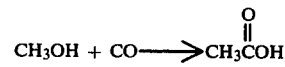

This reaction with a catalyst consisting of a soluble Rhodium species and an iodide promoter, (Rh-I), was first described in U.S. Pat. No. 3,769,329 by Monsanto (October 1973). The reaction is carried out at 180° C. and 500–1000 psi CO. The rate to acetic acid is about 20 $Mhr^{-1}$. The selectivity is exceptionally high, typically greater than 95%. At column 6, line 69, it is stated that use of a carbon monoxide and $H_2$ gas mixture will have no adverse effects on selectivity to acetic acid. Further, it is stated at column 9, starting on line 39, that a wide range of $H_2$: CO feed gas can be employed with no production of aldehydes from alcohols (that is, hydroformylation does not occur, only carbonylation). Example 5, clearly demonstrates that with $H_2$: $CO=38:62$ to 66:33 a Rh-I catalyst at 175° C. converts methanol only to acetic acid; it is clearly stated that acetaldehyde is not produced. Additionally, in a recent literature publication by R. T. Eby and T. C, Singleton (Applied Industrial Catalysis, Volume I, page 275, 1983), it is stated on page 293 that high $H_2$ partial pressures enhance propionic acid formation in the Rh-I catalyzed carbonylation of methanol. Again, acetaldehyde is not reported as a product when a Rh-I catalyst is utilized with a CO and $H_2$ mixture and methanol.

Finally, in GB 1584740 to Air Products (February, 1981) a methanol, carbonylation catalyst consisting of $Rh-I-R_2E(CH_2)n\ ER_2$ where $E=P$ or As and R is an organic moiety was disclosed. The reaction is carried out at 190° C. and 750 psi CO. Acetic acid rates and selectivities are 1.0 $Mhr^{-1}$ and 95%. There was no mention of the use of this catalyst with synthesis gas and methanol nor was the production of acetaldehyde disclosed.

SUMMARY OF THE INVENTION

A method of synthesizing aldehydes has now been found which comprises contacting a primary alcohol having the formula ROH wherein R is an alkyl group having 1 to about 20 carbon atoms, a cycloalkyl group having 4 to about 7 carbon atoms, or an aralkyl group having about 6 to about 18 carbon atoms, with a mixture of carbon monoxide and hydrogen at a temperature of about 100° C. to about 300° C. under superatmospheric pressure in the presence of a catalyst consisting of a soluble rhodium containing compound, an iodide containing compound and a chelating compound having the generic formula:

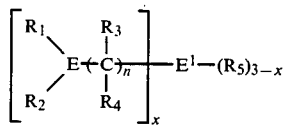

wherein each of $R_1$, $R_2$, $R_3$, $R_4$ and $R_5$ is an organic moiety or hydrogen and can be alike or different, E and $E^1$ are each Group V elements, n is an integer having values of 1 to about 4, and x is an integer having values of 1 to 3 inclusive, for a period of time sufficient to produce a primary aldehyde having the formula, RCHO.

The catalysts of this invention are obtained by the interaction of a soluble rhodium containing compound, an iodide containing compound, a chelating compound as defined above and optionally a mixture of chelating compound and monodentate compound having the generic formula:

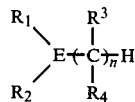

where E is N, P, As, Sb, or Bi and each of $R_1$, $R_2$, $R_3$ and $R_4$ is as defined above.

This is the first homogeneous rhodium-based catalyst capable of generating acetaldehyde via the hydroformylation of methanol.

DESCRIPTION OF THE INVENTION

The primary alcohols used as substrates for the production aldehydes in the present invention can be saturated aliphatic alcohols, such as, methanol, ethanol, n-propanol, n-butanol, n-pentanol, n-hexanol, and the like; saturated cycloaliphatic alcohols, such as, cyclobutanol, cyclopentanol, cyclohexanol, cyclohexanol, and the like; or aromatic alcohols, such as benzyl alcohol, 2-phenylethanol, and the like.

The saturated aliphatic alcohols are preferred substrates with methanol being the most preferred.

The catalyst used in the claimed method is stable, has a high activity or conversion rate, and has a high selectivity for the production of aldehydes from the corresponding alcohols.

Stability of the catalyst relates to how long the catalyst remains functional before either breaking down or losing its catalytic effect.

Activity or conversion rate relates to the amounts of reactants the catalyst converts to product per unit of time, generally expressed in g. mole per liter per hour (g. mole/l/hr).

Selectivity relates to the quantity of desired product produced, generally expressed in mole percent, based on the total amount of both desired products and undesired products produced.

The essential rhodium component of the catalyst system of the present invention may be provided by introducing into the carbonylation reaction zone a compound of rhodium. Among the materials which may be charged to the reaction zone to provide the rhodium component of the catalyst system of the present invention are rhodium metal, rhodium salts and oxides, organo rhodium compounds, coordination compounds of rhodium, and the like. Specific examples of materials capable of providing the rhodium constituent of the catalyst system of the present invention may be taken from the following non-limiting partial list of suitable materials.

$RhCl_2$
$RhBr_2$
$RhI_2$
$RhCl_3 \cdot 3H_2O$
$RhBr_3 \cdot 3H_2O$
$Rh_2(CO)_4Cl_2$
$Rh_2(CO)_4Br_2$
$Rh_2(CO)_4I_2$
$Rh_2(CO)_8$
$Rh[(C_6H_5)_3P]_2(CO)I$
$Rh[(C_6H_5)_3P]_2(CO)Cl$
Rh metal
$Rh(NO_3)_3$
$RhCl[(C_6H_5)_3P]_2(CH_3I)_2$
$Rh(SnCl_3)[(C_6H_5)_3P]_2$
$RhCl(CO)[(C_6H_5)_3As]_2$
$RhI(CO)[(C_6H_5)_3Sb]_2$
$[(n—C_4H_9)_4P][Rh(CO)I_4]$
$Rh[(C_6H_5)_3P]_2(CO)Br$
$Rh[(n—C_4H_9)_3P]_2(CO)Br$
$Rh[(n—C_4H_9)_3P]_2(CO)I$
$RhBr[(C_6H_5)_3P]_3$
$RhI[(C_6H_5)_3P]_3$
$RhCl[(C_6H_5)_3P]_2$
$RhCl[(C_6H_5)_3P]_3H_2$
$[(C_6H_5)_3P]_3Rh(CO)H$
$Rh_2O_3$
$[Rh(C_3H_4)_2Cl]_2$
$K_4Rh_2Cl_2(SnCl_2)_4$
$K_4Rh_2Br_2(SnBr_3)_4$
$K_4Rh_2I_2(SnI_2)_4$ The mole ratio of rhodium to alcohol can vary over a wide range. Enough rhodium must be used to achieve reasonable reaction rates, however, excess rhodium (such that its solubility under reaction conditions is greatly exceeded) is not advantageous. A variety of rhodium sources can be used such as carboxylates, carbonyls, halides, dimers, or complexes of the type $Rh(C_5H_7O_2)[A_2E(X)EA_2]$ or $Rh(CO)(I)[A_2E(X)EA_2]$ where E's are alike or different and are P, N, or As; and X is an organic moiety connecting the $A_2E$ groups. X can be a simple $(CR_2)_n$ group where R is an organic moiety or hydrogen. X can be a complicated bridging the group such as 1,2-C$_6$R$_4$. A's are alike or different and are hydrogen, aliphatic, aromatic, or cycloaromatic moieties or (CR$_2$)$_m$ER$_2$, where m=1 to 5, E=P, N or As, and R's are alike or different and are hydrogen, aliphatic, aromatic, or cycloaliphatic moieties. Mixtures or rhodium compounds can be used. The preferred rhodium to alcohol molar ratio is about 1:100 to 1:1000 although, it can vary from 1:25 to 1:20,000 with the most preferred range being from about 1:100 to 1:500. The amount used is not a critical feature in this invention and higher rhodium concentrations are acceptable but are influenced by economic considerations.

Iodide can be provided to the system from a number of sources including iodine; hydroiodic acid; methyl iodide and other organic iodides such as acetyl iodide, ethyl iodide and the like; alkali and alkaline earth iodides such as potassium iodide, lithium iodide, or calcium iodide; ammonium salts such as ammonium iodide, methyl ammonium iodide, and tetramethyl ammonium iodide; phosphonium salts such as triphenylphosphonium iodide, tricyclohexylphosphonium iodide, tri-p-tolylphosphonium iodide, or methyl triphenylphosphonium iodide.

The iodide to rhodium ratio can vary over a wide range. The preferred molar ratios are I:Rh=500:1 to 1:10, the most preferred being 100:1 to 1:5.

Typical examples of preferred chelating compounds are:

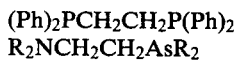

(Ph)$_2$PCH$_2$CH$_2$P(Ph)$_2$
R$_2$NCH$_2$CH$_2$AsR$_2$

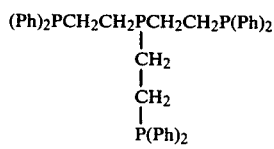

(Ph)$_2$PCH$_2$CH$_2$PCH$_2$CH$_2$P(Ph)$_2$
|
CH$_2$
|
CH$_2$
|
P(Ph)$_2$

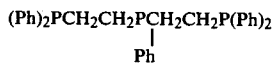

(Ph)$_2$PCH$_2$CH$_2$PCH$_2$CH$_2$P(Ph)$_2$
|
Ph where Ph=phenyl.

The preferred chelating compounds correspond to the generic formula:

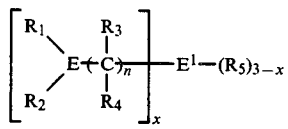

when x is 1, 2 or 3 respectively. These are represented by the following sub-generic formulae:

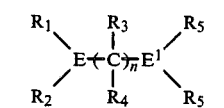
I.

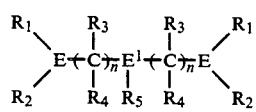
II.

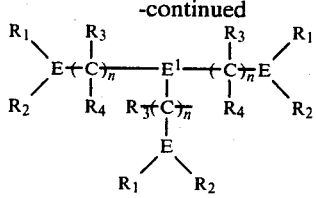
III.

Other examples of chelating compounds include:
bis(diphenylphosphino)methane,
bis(diphenylphosphino)propane,
bis(diphenylphosphino)butane,
bis(dicyclohexylphosphino)ethane,
bis(diphenylphosphinoethyl)phenylphosphine,
tris(2-diphenylphosphinoethyl)phosphine,
bis(di-p-tolylphosphino)ethane,
bis(1,2-diphenylphosphino)benzene,
bis(1,1-diphenylphosphino)-1-methylmethane,
bis(diphenylarsino)ethane,
1-diphenylphosphino-2-diphenylarsinoethane,
N,N'-phenylethylenediamine,N,N'-diphenylethylenediamine, and
N,N,N',N'-tetramethylphenylenediamine and the like.

The preferred molar ratio of chelating compound: Rh is 1:50 to 50:1, the most preferred being 1:10 to 10:1.

It is also possible to run a mixture of chelating compound and ER$_3$ where ER$_3$ is a Group VP monodentate compound. In the case of ER$_3$, E is N, P, or As and R is an organic moiety. The compound can be symmetrically or unsymmetrically substituted with R. Examples of the monodentate ER$_3$ compounds include triphenylphosphine, tricyclohexylphosphine, tri-p-tolylphosphine, tributylphosphine, propyldiphenylphosphine, tri-p-tolylphosphine, tributylphosphine, propyldiphenylphosphine, dipropylphenylphosphine, ethyldipropylphosphine, phosphine oxides, phosphites, and amines and arsines of the same type as the phosphine described above.

REACTION CONDITIONS

The catalytic process is carried out at temperatures of 100° C. to 300° C., preferably 140° C. to 220° C., and pressures of 100 to 10,000 psi, preferably 500 to 3,000 pri. The H$_2$ to CO ratio can range from 10:1 to 1:10.

A solvent is optional, however, in some cases a solvent can be beneficial to the process. A number of materials can be used as inert diluents in this process. Materials such as aprotic amides or imides or an aprotic heterocyclic compound containing an —O—C(O) grouping in the ring, such as N-methyl-2-pyrrolidinone, are preferred. 1,4-Dioxane, polyethylene glycols R—OCH$_2$CH$_2$[O—CH$_2$CH$_2$]$_n$—OR and their mono- and dicapped ethers where n≧0 and R's are alike or different and are hydrogen, aliphatic, aromatic, or cycloaromatic groups such as methyl, ethyl, butyl, phenyl, or cyclohexyl, and the like, diphenyl ether, sulfolane, tripropylphosphine oxide, and toluene are also acceptable, while in some cases they appear to be reactive and/or lead to two-phase product systems which might be difficult to manipulate in a commercial process.

The solvent:alcohol volume ratio should be from 20:1 to 1:20.

The invention is further described in the examples which follow. All parts and percentages are by weight unless otherwise specified.

EXPERIMENTAL PROCEDURES

Procedure I

All reactions were carried out in a 300 cc reaction autoclave constructed of Hastelloy C. The autoclave is equipped with a magnetically driven agitator, internal cooling coil, gas sampling port and electric heater. Prior to charging the reactants, the autoclave is washed with methanol at 100° C. at 500–1,000 psi syn gas for 30 minutes. The reactor is drained, opened, rinsed with acetone, and dried with nitrogen. To the open and cleaned reactor is charged first the liquid and then the solid reactants. The reactor is closed, purged with syn gas and then pressured to 500 psi with syn gas. With agitation (750 rpm's), the reactor contents are heated to the prescribed temperature, usually between 160°–180° C. in about 45 minutes. As soon as the temperature has been reached, the reactor is brought to the desired pressure plus 250 psi. The reaction is allowed to consume gas until the pressure has fallen to 250 psi below the desired pressure. The reaction is then repressurized. One such cycle is considered 500 psi gas uptake. Unless otherwise specified reactions were allowed to proceed for 1.0 hour.

At the end of an experiment, the reactor contents are normally cooled to 10° C. A vapor phase sample is taken and analyzed by gas chromatography for CO, $H_2$, $CO_2$, and $CH_4$ plus other gaseous hydrocarbons. The reactor gas phase is vented through two dry ice-acetone traps and then a 2.5 gallon saturated solution of calcium hypochlorite to remove iron and/or nickel carbonyls. The reactor is pressurized three times with 90 psi nitrogen and vented through the same trap-vent system.

The reactor contents are dumped into a chilled pressure bottle and crown capped. The liquid products are analyzed with a Hewlett-Packard 5880 gas chromatograph, equipped with two columns of ⅛"×10 Chromosorb 101 60/80 mesh which are connected in series with a ⅛" union tube.

PROCEDURE II

Reactions were carried out in a 150 cc autoclave constructed of 316 stainless steel. The autoclave is equipped with a magnetically driven agitator, external cooling, external steam heating, external electric heating, and gas and liquid sampling ports. Prior to charging the reactants, the autoclave is washed sequentially with tetraglyme and acetone at 180° C. and 1000 psi syn gas for 30 minutes. The reactor is drained, opened, disassembled, scrubbed, rinsed with water and acetone, and dried with nitrogen. The cleaned reactor is charged under an argon atmosphere with a premixed (under argon) solution of alcohol, rhodium compound, and chelating and monodentate (optional) compounds. The iodide compound is then charged. The reactor is sealed under an argon atmosphere and pressurized with syn gas to 300 psi. With agitation, the reactor contents are heated to the prescribed temperature, usually 150° to 200° C., in about 30 minutes. As soon as the temperature has been reached, the reactor is brought to the desired pressure plus 100 psi. The reaction is allowed to consume gas until the pressure has fallen to 100 psi below the desired pressure. The reaction is then repressurized. One such cycle is considered 200 psi gas uptake. Unless otherwise specified, reactions were allowed to proceed for five hours.

At the end of the experiment, the reactor contents are cooled to 25° C. A vapor phase sample is taken and analyzed by gas chromatography for CO, $H_2$, $CO_2$, and $CH_4$ plus other gaseous hydrocarbons. The reactor gas phase is then vented, and repressurized with 90 psi nitrogen and vented three times to remove metal carbonyls and carbon monoxide.

The reactor contents are dumped under nitrogen into a bottle and capped. The liquid product is analyzed at subambient temperatures using a Varian 3700 gas chromatograph equipped with a 30 meter capillary Durabond 1701 FSOT column.

CONTROL A

The autoclave was charged with the following components:

8.0 mm $Rh(CO)_2(C_5H_7O_2)$ ($C_5H_7O_2$=acetyl acetonate)
16.0 mm $I_2$
20.0 mm $PPh_3$
150.0 mL $CH_3OH$
no chelating ligand

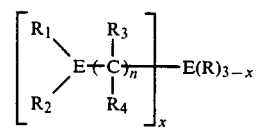

Following Procedure I, described above, the reactor was heated to 180° C. and the pressure adjusted to 1500 psi using a $H_2$:CO ratio of 1:1. The reaction was run to 30% methanol conversion. The rates and selectivities to acetaldehyde and methyl acetate are shown as entry #1 in Table 1. The remainder of the product mixture consisted of unreacted methanol and small amounts of acetic acid and dimethyl ether. This control shows that low rate and selectivity to acetaldehyde from methanol are obtained when a monodentate $ER_3$ compound is used in the absence of a chelating ligand

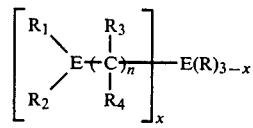

EXAMPLE 1

This example is the same as Control A with the exception that 10.0 mmole of $Ph_2PCH_2CH_2PPh_2$ was used in place of $PPh_3$. The rates and selectivities to acetaldehyde and methyl acetate are shown as entry #2 in Table I. Other products are the same as in Control A. This example shows the significant improvement in rate and acetaldehyde selectivity when a chelating phosphine compound is used in place of a monodentate phosphine compound. High rates and selectivities to acetaldehyde attainable using a rhodium-iodide-chelating ligand catalyst under low pressure of syn gas. Similar productivities are not possible with a cobalt catalyst at these reaction conditions.

EXAMPLE 2

This example is the same as Control A with the exception that 10.0 mm of $Ph_2AsCH_2CH_2AsPh_2$ was used in place of $PPh_3$. The rates and selectivities to acetaldehyde and methyl acetate are shown as entry #3 in Table I. Other products are the same as in Control A. This example shows that chelating arsine compounds are also superior for acetaldehyde production compared to monodentate phosphine compounds.

EXAMPLE 3

This example is the same as Control A except that 10.0 mmoles of PhN(H)CH$_2$CH$_2$N(H)Ph was used in place of PPh$_3$. The rates and selectivities to acetaldehyde and methyl acetates are shown as entry #4 in Table I. Other products are the same as in Control A. This example shows that chelating amine compounds are superior for acetaldehyde production compared to monodentate phosphine compounds. The chelating amine compound exhibits similar rates and selectivities to the chelating arsine compound.

EXAMPLE 4

The autoclave was charged with the following components:

8.0 mm Rh(CO)$_2$(C$_5$H$_7$O$_2$)
20.0 mm I$_2$
8.0 mm P(CH$_2$CH$_2$PPh$_2$)$_3$
150.0 mL CH$_3$OH

Following Procedure I, described above, the reactor was heated to 180° C. and the pressure adjusted to 1500 psi using a H$_2$:CO ratio of 1:1. The reaction was run to 30% methanol conversion. The rates and selectivities to acetaldehyde and methyl acetate are shown as entry #5 in Table I. The remainder of the product mixture consisted of unreacted methanol and small amounts of acetic acid and dimethyl ether.

This example shows the rates and selectivities to acetaldehyde approach those observed with a solvent-free Co-I-PPh$_3$ catalyst, which must be run under higher pressures (i.e., 3000 psi).

CONTROL B

The autoclave was charged with the following components:

4.0 mm Rh(CO)$_2$(C$_5$H$_7$O$_2$)
16.3 mm CH$_3$CH$_2$I
8.0 mm PPh$_3$
75 mL CH$_3$CH$_2$OH

Following Procedure II, described above, the reactor was heated to 180° C. and the pressure adjusted to 2000 psi using a H$_2$:CO ratio of 1:1. The rates and selectivities to propionaldehyde (including propionaldehyde diethyl acetal) and ethyl propionate are shown as entry #1 in Table II. The remainder of the product mixture consisted of unreacted ethanol, ethyl iodide, and di-ethyl ether. Control B shows the low rate and selectivity to propionaldehyde when a monodentate Group V compound is used.

EXAMPLE 5

This example is the same as Control B except that 4.0 mmole of Ph$_2$PCH$_2$CH$_2$PPh$_2$ was used in place of PPh$_3$. The rates and selectivities to propionaldehyde (including propionaldehyde diethyl acetal) and ethyl propionate are shown as entry #2 in Table II. The remainder of the product mixture was the same as in Example 67. This example shows the improvement in rate and selectivity to propionaldehyde when a chelating phosphine compound is used in place of a monodentate phosphine compound. That is, ethanol can be hydroformylated to propionaldehyde under low syn gas pressure using a rhodium-iodide chelating ligands catalyst.

TABLE I
METHANOL HYDROFORMYLATION

| | | | CH$_3$CHO | | CH$_3$C(O)OCH$_3$ | |
|---|---|---|---|---|---|---|
| # | Compound | $^a$Rate | $^b$Selectivity | Rate | $^b$Selectivity | |
| 1 | PPh$_3$ | 0.1 | 2 | 5.0 | 93 |
| 2 | Ph$_2$PCH$_2$CH$_2$PPh$_2$ | 5.0 | 50 | 3.0 | 30 |
| 3 | Ph$_2$AsCH$_2$CH$_2$AsPh$_2$ | 1.0 | 20 | 1.6 | 50 |
| 4 | PhN(H)CH$_2$CH$_2$N(H)Ph | 1.0 | 30 | 2.0 | 60 |
| 5 | P(CH$_2$CH$_2$PPh$_2$)$_3$ | 2.2 | 70 | | |

$^a$Mhr$^{-1}$
$^b$weight percent of liquid products

TABLE II
ETHANOL HYDROFORMYLATION

| | | CH$_2$CH$_3$CHO | | CH$_3$CH$_2$C(O)OCH$_2$CH$_3$ | |
|---|---|---|---|---|---|
| # | Compound | $^a$Rate | $^b$Selectivity | $^a$Rate | $^b$Selectivity |
| 1 | PPh$_3$ | 0.01 | 1.6 | 0.12 | 24.8 |
| 2 | Ph$_2$PCH$_2$CH$_2$PPh$_2$ | 0.16 | 13.6 | 0.33 | 49.4 |

$^a$Mhr$^{-1}$
$^b$weight percent of liquid products

EXAMPLE 6

A series of experiments were carried out with various chelating ligands. In all cases the following amounts were employed:

Rh(CO)$_2$C$_5$H$_7$O$_2$ = 8.0 mm
I$_2$ = 16.0 mm
Chelating Ligand = 10.0 mm
CH$_3$OH = 150 mL Each run was carried out at 180° C. and 1500 psi (H$_2$:CO = 1:1) according to Procedure I. The methanol conversion was 30%. The results are summarized below:

| | | | CH$_3$CHO | CH$_3$C(O)OCH$_3$ | |
|---|---|---|---|---|---|
| # | ER$_3$ Compound | $^a$Rate | $^b$Selectivity | Rate | $^b$Selectivity |
| 1 | None | 0.0 | 0 | 10.0 | 95 |
| 2 | Ph$_2$—P—CH$_2$—PPh$_2$ | 0.5 | 20 | 5.0 | 70 |
| 3 | Ph$_2$—PCH$_2$—CH$_2$—PPh$_2$ | 5.0 | 50 | 3.0 | 30 |
| 4 | Ph$_2$—PCH$_2$—CH$_2$—CH$_2$—PPh$_2$ | 6.1 | 30 | 14.0 | 62 |
| 5 | Ph$_2$—PCH$_2$—CH$_2$—CH$_2$—CH$_2$—PPh$_2$ | 0.2 | 5 | 4.0 | 86 |
| 6 | (C$_2$H$_5$)$_2$—PCH$_2$—CH$_2$—P(C$_2$H$_5$)$_2$ | 0.1 | 5 | 3.0 | 85 |
| 7 | (p-CH$_3$C$_6$H$_4$)$_2$PCH$_2$CH$_2$P(p-CH$_3$C$_6$H$_4$)$_2$ | 4.0 | 55 | 2.8 | 50 |
| 8 | (C$_6$H$_{11}$)$_2$PCH$_2$CH$_2$P(C$_6$H$_{11}$)$_2$ | 2.1 | 40 | 4.0 | 49 |

| # | ER₃ Compound | $^a$Rate | CH₃CHO $^b$Selectivity | Rate | CH₃C(O)OCH₃ $^b$Selectivity |
|---|---|---|---|---|---|
| 9 | 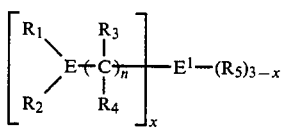 | 2.5 | 22 | 3.0 | 68 |

$^a$Mhr$^{-1}$
$^b$weight percent of liquid products

Other products are similar to Control A.

Run #1 was carried out with no chelating ligand and generated only methyl acetate as excepted from prior art reported by Monsanto.

Runs 2-5 demonstrate the effect of varying n in Ph₂P(CH₂)$_n$PPh₂ from 1 to 4. All values for n work, however, n=2 and 3 are best with n=2 being the most preferred. Run #3 is the same as Example 1.

Although the invention has been described in its preferred forms with a certain degree of particularity, it is understood that the present disclosure has been made only by way of example and that numerous changes can be made without departing from the spirit and the scope of the invention.

We claim:

1. Method of synthesizing aldehydes which comprises contacting a primary alcohol having the formula, ROH, wherein R is an alkyl group having 1 to about 20 carbon atoms, a cycloalkyl group having 4 to about 7 carbon atoms, or an aralkyl group having about 6 to about 18 carbon atoms, with a mixture of carbon monoxide and hydrogen at a temperature of about 100° C. to about 300° C. under superatmospheric pressure in the presence of a catalyst consisting essentially of a soluble rhodium containing compound, an iodide containing compound and a chelating compound having the generic formula:

$$\left[ \begin{array}{c} R_1 \\ \diagdown \\ \diagup \\ R_2 \end{array} E \!\!-\!\!\! \left( \begin{array}{c} R_3 \\ | \\ C \\ | \\ R_4 \end{array} \right)_{\!\!n} \!\!-\!\! E^1 \!\!-\!\! (R_5)_{3-x} \right]_x$$

wherein each of $R_1$, $R_2$, $R_3$, $R_4$ and $R_5$ is an organic moiety or hydrogen and can be alike or different, E and $E^1$ are each Group V elements, n is an integer having values of 1 to about 4, and x is an integer having values of 1 to 3 inclusive, for a period of time sufficient to produce a primary aldehyde having the formula, RCHO.

2. Method claimed in claim 1 wherein the primary alcohol is methanol.

3. Method claimed in claim 1 wherein the primary alcohol is ethanol.

4. Method claimed in claim 1 wherein the rhodium to alcohol molar ratio is about 1:100 to about 1:1000.

5. Method claimed in claim 1 wherein the molar ratio of carbon to hydrogen is about 10:1 to about 1:10.

6. Method claimed in claim 1 wherein the iodide to rhodium molar ratio is about 500:1 to about 1:10.

7. Method claimed in claim 1 wherein the $R_1$, $R_2$, $R_3$, $R_4$ and $R_5$ groups are selected from the class consisting of hydrogen, saturated aliphatic or cycloaliphatic moieties and aromatic moieties.

8. Method claimed in claim 1 wherein the $R_1$, $R_2$, $R_3$, $R_4$ and $R_5$ groups are phenyl.

9. Method claimed in claim 1 wherein E and $E^1$ are non-metals selected from the group consisting of phosphorus, nitrogen or arsenic.

10. Method claimed in claim 1 wherein E and $E^1$ are phosphorus.

11. Method claimed in claim 1 wherein part of the chelating compound is replaced by a monodentate moiety having the formula $E(R_1)_3$ where E and $R_1$ are as defined above.

12. Method claimed in claim 1 wherein the temperature is about 140° C. to about 220° C.

13. Method claimed in claim 1 wherein the pressure is about 100 psi to about 10,000 psi.

14. Method claimed in claim 1 wherein the pressure is about 500 to about 3000 psi.

15. Method claimed in claim 1 wherein a solvent is used.

16. Method claimed in claim 15 wherein the solvent:alcohol volume ratio is in the range of about 20:1 to 1:20.

17. Method claimed in claim 1 wherein the iodide moiety is derived from I₂.

18. Method claimed in claim 1 wherein the integer n has a value of 1.

* * * * *